United States Patent [19]
Christofel et al.

[11] Patent Number: 5,970,979
[45] Date of Patent: Oct. 26, 1999

[54] DEVICE AND METHOD FOR MAINTAINING AN OPEN POUCH STRUCTURE

[76] Inventors: Donna L. Christofel, 9414 Lincolnwood Dr., Evanston, Ill. 60203; Joseph F. Thompson, 882 Wylde Oak Dr., Oshkosh, Wis. 54904

[21] Appl. No.: 08/596,844

[22] Filed: Feb. 5, 1996

[51] Int. Cl.[6] .................................................. A61B 19/00
[52] U.S. Cl. ................................................ 128/849; 128/853
[58] Field of Search .......................... 128/849, 856, 128/DIG. 24

[56] References Cited

U.S. PATENT DOCUMENTS

| | | | |
|---|---|---|---|
| 4,169,472 | 10/1979 | Morris | 128/132 D |
| 4,890,628 | 1/1990 | Jackson | 128/849 |
| 5,038,798 | 8/1991 | Dowdy | 128/853 |
| 5,107,859 | 4/1992 | Alcorn et al. | 128/853 |
| 5,143,091 | 9/1992 | Patnode | 128/853 |
| 5,322,071 | 6/1994 | Ambrose | 128/853 |

*Primary Examiner*—Michael A. Brown

[57] ABSTRACT

The invention comprises a fluid collection pouch for use during surgical procedures to collect fluids and surgical debris. It comprises a flexible fluid retaining bag having an open top fitted with a flexible, compressible multi-channeled rib. The multi-channeled rib allows fluid to enter the bag even if accidentally closed.

3 Claims, 2 Drawing Sheets

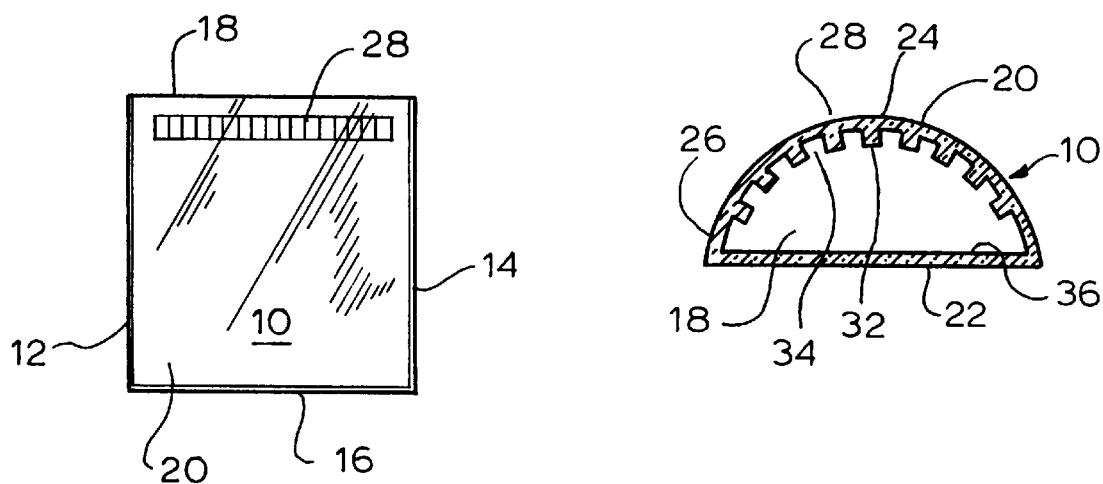
FIG. 1
FIG. 2
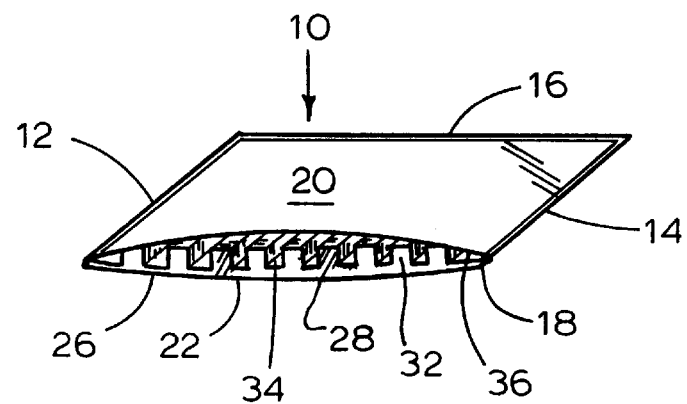
FIG. 3

DEVICE AND METHOD FOR MAINTAINING AN OPEN POUCH STRUCTURE

FIELD OF THE INVENTION

The invention relates to pouches or bags used in connection with a drape to collect fluids produced and used in surgical procedures.

BACKGROUND OF THE INVENTION

Prior to surgery, patients have the surgical area draped with a surgical drape. Often associated with these drapes are fluid collection bags. These bags are most often used in operations where large amounts of fluid runoff is anticipated. The bags or pouches, which terms are used herein synonymously, are usually attached to the drape in such a way as to collect fluid run off. In addition the drape may or may not have construction features which serve to channel the fluids into the bag.

A problem associated with these pouches is that after they are opened to receive and collect fluids they are often times closed accidentally during the surgical procedure being performed. These undesirable closures can be caused by physical contact with operating room personnel or equipment. When such unwanted closures occur, fluid associated with the surgery no longer is collected in the bags thereby spilling into unwanted areas and onto apparel and possibly contaminating the operating area. With the increased significance of deadly disease being transmitted through blood and bodily fluids, the importance of this problem is correspondingly increased. A good description of surgical drapes and fluid collection bags associated therewith is presented in U.S. Pat. No. 5,107,859, which is incorporated herein by reference.

It was sought to maintain these prior art bags in the open position using relatively rigid attachments such as wires or metal bars. Another proposed solution to the problem of unwanted bag closure was the use of reticulated porous foams positioned in the top of a bag's opening. Such embodiments attempted to use the pores of the foam as a means for allowing liquid passage when bag closure took place. These pores were often inadequate to pass or retain large volumes of liquid. Also, some prior art devices used to maintain these bags in the open position are often times not sufficiently resistant to compression forces of the type described to resist closure.

THE INVENTION

To overcome the disadvantages associated with the prior art, the invention herein comprises a fluid collection pouch for use during surgical procedures to collect fluids and surgical debris. The pouch is constructed to eliminate the possibility of accidental closure under conceivable operating room circumstances and to receive fluids even when the forces that would have caused accidental closure have occurred. In the preferred embodiment the pouch comprises a flexible fluid retaining pocket-like structure having front and back panels whose sides and bottom are sealed. It has an open top which has fitted to an edge thereof an elongated flexible, partially compressible multi-channeled rib. The channels extend transverse of the length and preferably are U shaped, with the bottom of the U being flat. The multi-channeled rib is dimensioned to fit along substantially the length of and in parallel relationship to an interior edge of the top. In practice we have found that it works well when it is at least ⅔ the length of the interior edge of the pouch and preferably it is the length of the interior edge of the top of the pouch. The multi-channeled rib, in a preferred embodiment of the invention, is fitted or attached to the inside of the top edge of the front panel, so that the channels oppose the edge of the top of the back panel. This configuration maximizes the capability of the pouch on the outer fluid receiving surface to receive fluids through the channels when accidental closure takes place. The ribs under normal conditions of use should compress to not more than about 90% of its original height. Preferably, the compression should not exceed 50%.

In another embodiment of the invention the multi-channeled rib may be fabricated in the shape of an arc which after attachment to the interior of the top edge of the front panel would keep the pocket in a normally open position. When this mode of the invention is contemplated it is beneficial to use so called "memory" plastics which return to their original shape after deformation. Such plastics are illustrated by the polymers: polyvinyl chloride, high impact polystyrene polyethylenes, polyesters, certain Nylon type polyamides, and polycarbonates which are a preferred species.

The individual ribs desirably are rectangular in configuration. The U shaped channels typically are ¹⁄₁₆" to about ½" wide and deep. The bottom of the channels may be either square or curved. The multi-channeled ribs may be cylindrical in over all configuration although this is not the most desirable shape.

The multi-channeled ribs may be attached to the pouch using adhesives or other attachment means. The choice of the adhesive will depend on the materials of construction of the pouch and the multi-channeled rib. The pouches are preferably constructed from clear plastic sheeting of such polymers as polyethylene, polypropylene and polyvinyl chloride. The pouches for the most part will be integral with or attached to a surgical drape using known methods of attachment compatible with the drape material. In certain cases it will be desirable to mount the bag in an appropriate area near the site of the proposed surgery. Since the multi-channeled rib is flexible it can be compressed to allow for easy packaging of the pouches either with surgical drapes or alone.

ADVANTAGES OF THE INVENTION

One advantage of the invention is that any manipulation of the pouch described or attachments is not required in order to function. Another advantage is even if the pouch is accidentally closed it is still capable of allowing fluids to be delivered to the pouch. A further advantage of the invention is that due to its inherent flexibility it may be incorporated into the construction of a surgical drape and be capable of being folded for packaging without disturbing the structure of the bag.

THE DRAWINGS

In the drawings;

FIG. 1 is a front vertical view showing the pouch of the invention;

FIG. 2 is a top view showing the pouch fitted with the multi-channeled rib in the open position;

FIG. 3 is a horizontal perspective view showing the pouch containing the multi-channeled rib in the closed position;

DETAILED DESCRIPTION OF THE INVENTION

Figure 4:
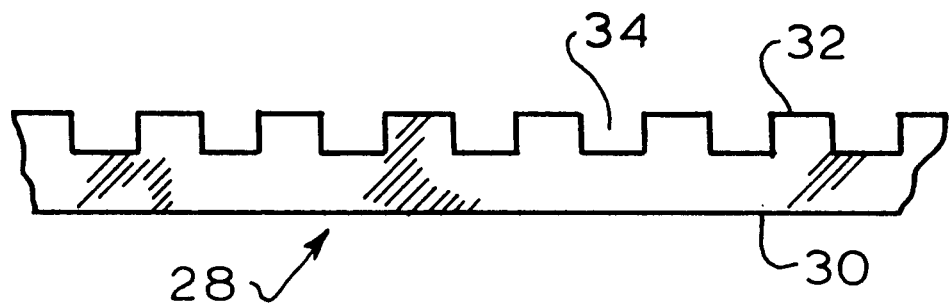
FIG. 4 is a side view of the multi-channeled rib.

As shown in FIG. 1 a pouch 10 of the invention has sealed sides 12 and 14 and a sealed bottom 16. Whatever the configuration, the pouch is fluid tight except for an open top 18 to which is fitted the means for maintaining the opening in a fluid receiving state under all circumstances. This assembly therefore joins together as a bag front panel 20 and a back panel 22. The interior, fluid collecting of the bag is designated by the numeral 24.

Figure 5:
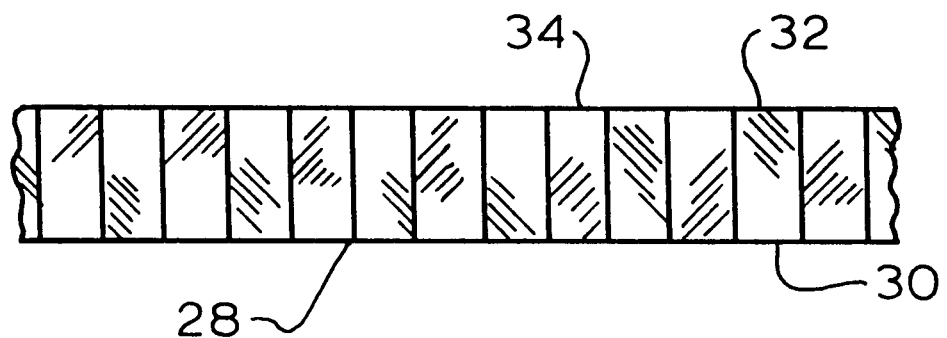
FIG. 5 is the top view corresponding to FIG. 4. In the drawings like parts have like numbers.

An inside edge 26 of the open top 18, which as shown is formed by the top of the front panel 20, is fitted with a multi-channeled rib structure 28 which is parallel to inside edge 26. As shown to best advantage in FIGS. 4 and 5, the multi-channeled rib structure 28 comprises a rectangular flat base 30 from which extends a plurality of protrusions or ribs 32. The spaces or notches between the ribs form channels 34 which are shown in FIGS. 4 and 5 to be of a squared U shape. It is to be noted that the length of the multi-channeled rib 28 corresponds generally to the length of the inside edge 26. The base 30 of the multi-channeled rib 28 is bonded to inside edge 26 of front panel 20. This positions the ribs 32 so that they oppose the inside edge 36 of back panel 22. This configuration represents a preferred embodiment of the invention.

As can be observed from FIGS. 1 and 2, when the pouch 10 is in the open position the multi-channeled rib 28 has an arcuate shape. It may be held in this position by means of stays such as wires or it may be constructed of a memory plastic in the form of the arc shown. In this case the multi-channel rib 28 maintains the pouch in an open fluid receiving position even when closing forces are exerted against the opening. When such forces are applied, the pouch assumes the configuration shown in FIG. 3. Even though in a state of compression, the channels 34 allow fluid to enter the pouch thus preventing an undesirable contamination of the operating site.

In practice we have found that the rib structure 28 may be advantageously made of expanded polyurethane or Styrofoam. In another embodiment the structure may be a bond of material such as coated metal or plastic bent in a tooled or notched configuration such as shown in FIG. 6.

Where the rib structure 28 is made of expanded foam, the density and configuration are such that all conceivable expected forces of persons pressing against the structure will not compress the structure so that the openings or notches are closed more than 50%. The qualities of the foam shall be such that even when the strongest conceivable forces will not be expected to reduce the openings or notches 34 by more than 90%.

Although the present invention has been described in detail with reference only to the presently preferred embodiments, it will be appreciated by those of ordinary skill in the art that various modifications can be made without departing from the spirit of the invention. Accordingly, the invention is limited only by the following claims.

What is claimed is:

1. A fluid collection pouch for use during surgical procedures to collect fluids and surgical debris which fluid collection pouch is capable of receiving fluids during periods of accidental closure comprising: a flexible fluid retaining bag with front and back panels and an open top having interior edges with the interior edge of the front panel being bonded along at least two-thirds of its length to the flat back of a flat backed linear flexible multi-channeled rib which is made of a high density plastic foam which under normal conditions of use compresses to not more than about 50%.

2. The fluid collection pouch of claim 1 where the channels are U shaped.

3. The fluid collection pouch of claim 1 where the flexible, compressible high density foam is a polyurethane foam.

* * * * *